United States Patent [19]

Isoyama et al.

[11] Patent Number: 5,263,979
[45] Date of Patent: Nov. 23, 1993

[54] ARTIFICIAL HEART

[75] Inventors: Takashi Isoyama, Tokyo; Kou Imachi, 5-2, Nishi 1-chome, Kamifukuoka City, Saitama Pref.; Iwao Fujimasa, 920-136, Mogusa, Hino City, Tokyo, all of Japan

[73] Assignees: Kou Imachi, Saitama; Iwao Fujimasa, Tokyo; Aisin Seiki Kabushiki Kaisha, Kariya, all of Japan

[21] Appl. No.: 8,848

[22] Filed: Jan. 25, 1993

Related U.S. Application Data

[63] Continuation of Ser. No. 854,071, Mar. 19, 1992, abandoned.

[30] Foreign Application Priority Data

Mar. 19, 1991 [JP] Japan .................. 3-078342

[51] Int. Cl.⁵ ............... A61M 1/10; A61N 1/362
[52] U.S. Cl. ..................... 623/3; 600/16; 600/17
[58] Field of Search ............ 623/2, 3; 600/16, 17; 417/393

[56] References Cited

U.S. PATENT DOCUMENTS 4,058,857 11/1977 Runge et al. .................. 623/3
4,888,011 12/1989 Kung et al. .................... 623/3
5,055,005 10/1991 Kletschka .................... 623/3 X Primary Examiner—Randall L. Green
Assistant Examiner—Dinh X. Nguyen
Attorney, Agent, or Firm—Sughrue, Mion, Zinn, Macpeak & Seas

[57] ABSTRACT

The invention is directed to an artificial heart having a pump, first and second pair of switching valves, and an electronic control unit which is arranged to control the valves to be actuated synchronously. When one of the first pair of valves and one of the second pair of valves are actuated to open, while the rest of them close, a blood from a right atrium is sucked and released by a pump through one of the first pair of valves, and subsequently, supplied into a pulmonary artery through one of the second pair of valves. At this time, a left atrium and an aorta are shut off, since the other ones of the first and second pair of valves are closed. Whereas, when the other ones of the first and second pair of valves are actuated to open while the rest of them close, the blood from the left atrium is sucked and released by the pump through the other of the first pair of valves, and subsequently, supplied into the aorta through the other of the second pair of valves. At this time, the right atrium and the pulmonary artery are shut off. By repeating these, the right and left systems of the heart operate alternately.

7 Claims, 2 Drawing Sheets

ARTIFICIAL HEART

This is a continuation of application Ser. No. 07/854,071 filed Mar. 19, 1992, now abandoned.

BACKGROUND OF THE INVENTION

1. Field of the Invention

The present invention relates to an artificial heart having a pulsation liquid pump, and more particularly to a device with a blood pump effective for a patient who cannot maintain a necessary blood circulation due to insufficient recovery of his own heart.

2. Description of the Prior Art

In order to assist a patient who cannot maintain a necessary blood circulation due to insufficient recovery of his own heart, various kinds of artificial hearts, such as a reciprocating pump-type artificial heart, a centrifugal pump-type artificial heart or the like, have been proposed as in Japanese Patent Laid-open Publication No. 59-28969, for example.

However, efficiencies of any prior artificial hearts are low, and their sizes and weights are large, so that they are not necessarily satisfactory ones which are to be internally inserted into patient bodies or to be carried. This is because the prior artificial hearts have been equipped with the pumps which are subject to discontinuous rotation or reciprocating motion for obtaining a pulsation liquid flow, and which cause efficiencies of actuators to be low, or because they have been required to have two pump chambers for left and right systems of the heart.

SUMMARY OF THE INVENTION

Accordingly, it is an object of the present invention to provide an artificial heart having a single pump for functioning with good efficiency in both left and right systems of the heart.

In accomplishing the above and other objects, an artificial heart according to the present invention comprises a pump for introducing a liquid through an inlet port and discharging the liquid from an outlet port, a first pair of switching valves connected to the inlet port of the pump for opening or closing a passage communicated thereto, a second pair of switching valves connected to the outlet port of the pump for opening or closing a passage communicated thereto, and means for controlling one of the second pair of switching valves to be actuated in synchronous relationship with one of the first pair of switching valves, and controlling the other of the second pair of switching valves to be actuated in synchronous relationship with the other of the first pair of switching valves.

Preferably, one of the first pair of switching valves is connected to a right atrium, and the other of the first pair of switching valves is connected to a left atrium, and one of the second pair of switching valves is connected to a pulmonary artery, and the other of the second pair of switching valves is connected to an aorta.

The first and second pair of switching valves may be formed in a valve mechanism which comprises a cylinder and a valve spool slidably disposed in the cylinder.

BRIEF DESCRIPTION OF THE DRAWINGS

The above stated object and following description will become readily apparent with reference to the accompanying drawings in which.

DESCRIPTION OF THE PREFERRED EMBODIMENT

Figure 1:
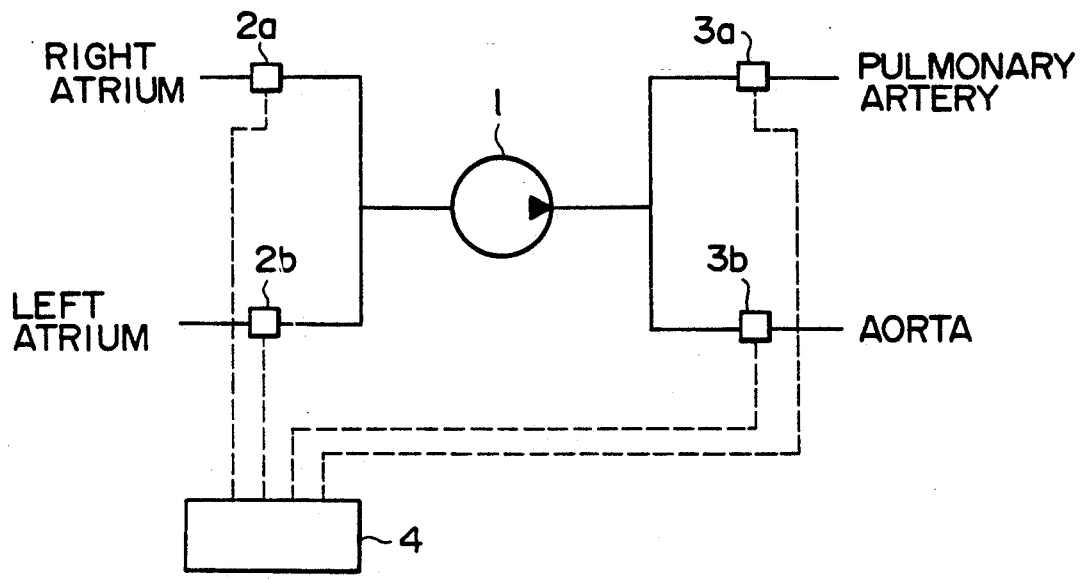
FIG. 1 is a block diagram of an artificial heart of an embodiment of the present invention.

Referring to FIG. 1, there is illustrated a block diagram of an artificial heart of an embodiment according to the present invention which includes a pump 1, a pair of switching valves 2a, 2b connected to an inlet side of the pump 1, a pair of switching valves 3a, 3b connected to an outlet side of the pump 1 and an electronic control unit 4 for controlling the valves 2a, 2b, 3a and 3b respectively. The control unit 4 is arranged to synchronously open or close one of the two valves 2a, 2b connected to the inlet side, and one of the two valves 3a, 3b connected to the outlet side, and synchronously open or close the other of the two valves 2a, 2b, and the other of the two valves 3a, 3b, respectively.

The pump 1 is a one-direction rotary liquid pump (e.g., a centrifugal pump manufactured by Bio Medicus Co.) driven by a motor (not shown), whose inlet side is connected to a right atrium and a left atrium through the switching valves 2a and 2b, respectively. The outlet side of the pump 1 is connected to a pulmonary artery and an aorta through the switching valves 3a and 3b, respectively. Each of the switching valves 2a, 2b, 3a and 3b is composed of an electromagnetic valve. The valve 2a out of the two valves 2a and 2b connected to the inlet side, and the valve 3a out of the two valves 3a and 3b connected to the outlet side, are controlled by the electronic control unit 4 so as to be synchronously opened and closed. The valve 2b and the valve 3b are also controlled to be synchronously opened and closed.

The artificial heart structured as described above operates as follows:

When the electronic control unit 4 is actuated to open the switching valves 2a and 3a and to close the switching valves 2b and 3b, the blood from the right atrium is sucked and released by the pump 1 through the valve 2a, and subsequently, supplied into the pulmonary artery through the valve 3a. At this time, passages to the left atrium and the aorta are shut off since the valves 2b and 3b are closed.

On the contrary, when the electronic control unit 4 is actuated to open the switching valves 2b and 3b and to close the switching valves 2a and 3a, the blood from the left atrium is sucked and released by the pump 1 through the valves 2b, and subsequently, supplied into the aorta through the valve 3b. At this time, passages to the right atrium and the pulmonary artery are shut off since the valves 2a and 3a are closed. By repeating these operations, a function for conducting a right system of the heart and a function for conducting a left system of the heart are exerted alternately.

In the above-described operation, it is preferable to change-over the valves 3a, 3b with a predetermined time delayed after changing-over the valves 2a, 2b, so as to reduce a blood mixture of the right and left system of the heart which might be caused in space and passages including the pump 1 disposed between the valves 2a, 2b and the valves 3a, 3b.

Figure 2:
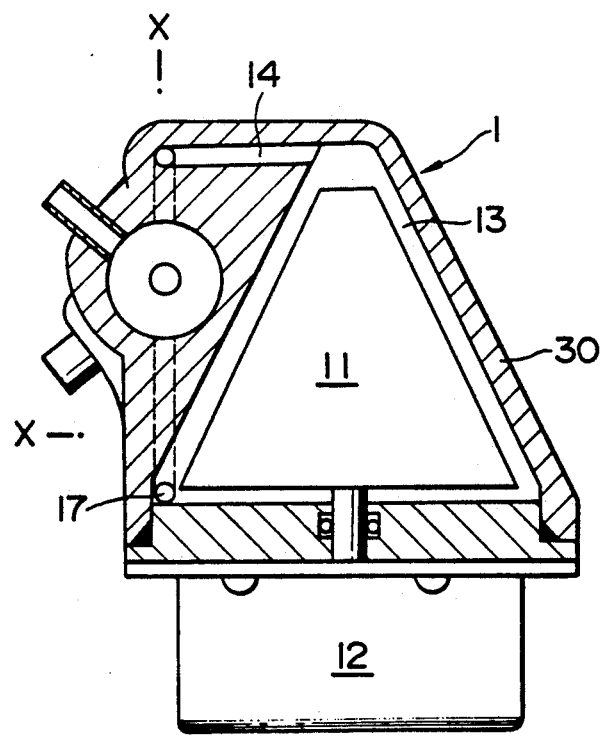
FIG. 2 is a sectional view of the artificial heart of the embodiment of the present invention.
Figure 3:
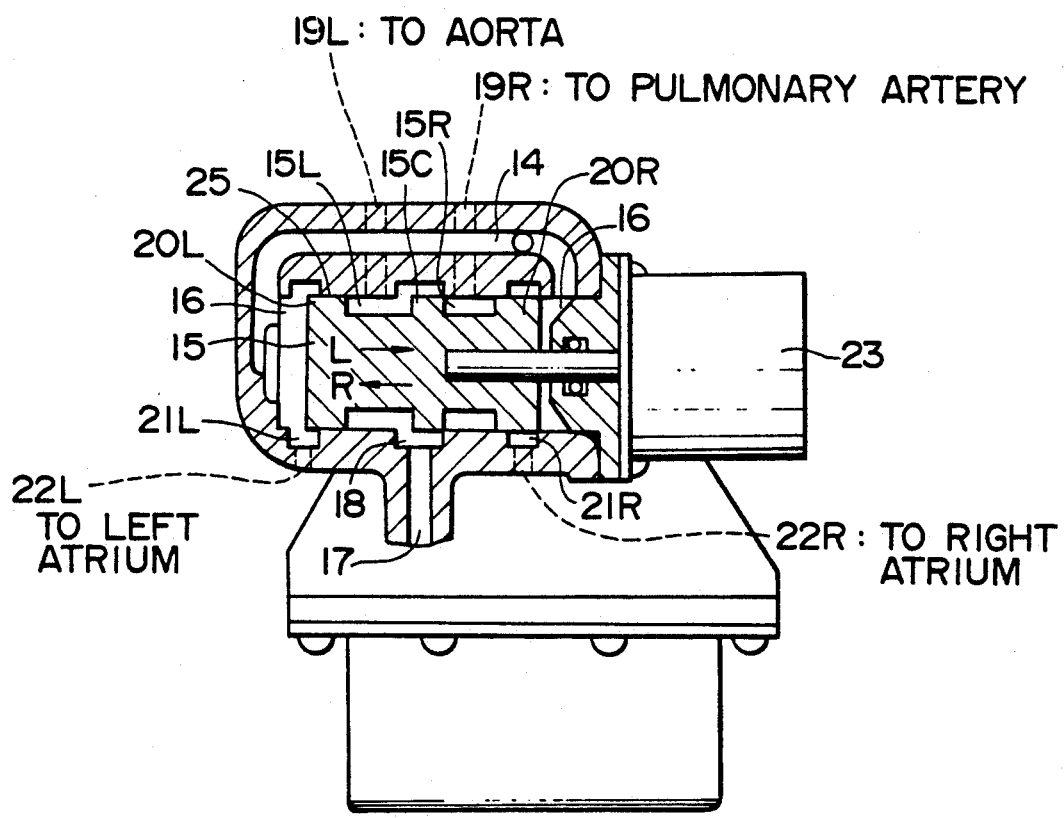
FIG. 3 is a sectional view of a valve mechanism in the embodiment of the present invention.

Referring now to FIGS. 2 and 3, the mechanisms of the pump 1 and the valves will be described in more details. In FIG. 2, the pump 1 is a centrifugal pump having a housing 30 and a rotor 11 which is disposed in a pump chamber 13 defined in the housing 30. The rotor 11 in the pump 1 is connected to a motor 12 through an axis. The rotor 11 and motor 12 may be disposed outside of a human body by connecting each other with a transfer cable. An upward center of the pump chamber 13 is connected to chambers 16, 16 defined at both ends of a valve spool 15, which will be described later, through an inlet port 14. A peripheral portion of the pump chamber 13 is connected to a center channel 18 (shown in FIG. 3) of a valve cylinder through an outlet port 17.

Then, referring to FIG. 3, the valve mechanism will be described. The valve mechanism includes a valve cylinder 25, a valve spool 15 slidably disposed within the valve cylinder 25, and an electromagnetic actuator 23 for actuating the valve spool 15 to reciprocate. This valve mechanism forms a 2-position type spool valve so that the valve spool 15 is positioned at either the right side or the left side in FIG. 3 within the valve cylinder 25.

The valve spool 15 is formed with channels 15L and 15R which are separated by a center land 15C formed on the valve spool 15. At a portion of the valve cylinder 25 facing the center land 15C, the outlet port 17 is formed through the center channel 18. In addition, ports 19L and 19R are formed respectively, at the portions of the valve cylinder 25 facing the channels 15L and 15R separated by the center land 15C. The port 17 is connected to the peripheral portion of the pump chamber 13, and the ports 19L and 19R are connected to the aorta and the pulmonary artery, respectively. Lands 20L and 20R are formed at both end portions of the valve spool 15 to define the channels 15L and 15R respectively, and also channels 21L and 21R are formed on the side of the valve cylinder 25 facing the lands 20L and 20R. The channels 21L and 21R are arranged to be connected to the left atrium and the right atrium through ports 22L and 22R respectively. One end of the valve spool 15 is connected to the electromagnetic actuator 23.

When the valve spool 15 moves in the direction indicated by an arrow L in FIG. 3 by means of the electromagnetic actuator 23 (i.e., when it is positioned in a state as shown in FIG. 3), the channel 21L communicates with the chamber 16 and the blood from the left atrium is sucked to the pump through the port 22L, channel 21L, chamber 16 and inlet port 14. At the same time, the channel 18 also communicates with the channel 15L, and the blood from the outlet port 17 is fed to the aorta through the channels 18 and 15L and the port 19L. On the other hand, the channel 21R communicating with the right atrium through the port 22R is separated by the land 20R from the chamber 16 and channel 15R to be shut off. The channel 15R communicating with the port 19R connected to the pulmonary artery is also separated by the land 15C from the channel 18 to be shut off. That is, a pumping operation from the left atrium to the aorta is performed, while passages to the right atrium and the pulmonary artery are shut off.

On the contrary, when the valve spool 15 moves in the direction indicated by an arrow R in FIG. 3, the operation is reversed, so that a pumping operation from the right atrium to the pulmonary artery is performed, while passages to the left atrium and the aorta are shut off. A holding time of the valve spool 15 to be positioned at each side thereof, that is, the period of either the function for conducting the left system of the heart or the function for conducting the right system of the heart is determined in accordance with biosystem so as to balance the output from the pump 1 to each system, e.g., the blood pressure in each atrium. That is, if the blood pressure in the right atrium becomes higher, or the blood pressure in the left atrium becomes lower, it means that the function for conducting the right system of the heart is getting weaker, and therefore, the period of the function for conducting the right system of the heart will be extended, and the period of the function for conducting the left system of the heart will be shortened.

The present embodiment of the invention is arranged to act for the functions for conducting both left and right systems of the heart. However, in case of assisting or acting for only one system of the heart, it can be easily realized by short-circuiting the inlet port of the valve 2a and the outlet port of the valve 3a, or short-circuiting the inlet port of the valve 2b and the outlet port of the valve 3b in FIG. 1. Furthermore, if a pump having an internal leakage such as a centrifugal pump is employed as the pump 1, the path at one side thereof, that is, either the path of the valves 2a and 2b or the path of the valves 3a and 3b may be omitted.

Thus, it should be apparent to one skilled in the art that the above-described embodiment is merely illustrative of but a few of the many possible specific embodiments of the present invention. Numerous and various other arrangements can be readily devised by those skilled in the art without departing from the spirit and scope of the invention as defined in the following claims.

What is claimed is:

1. An artificial heart for the circulatory system of a human body consisting essentially of:
    a single one-way pump configured to introduce blood through an inlet port and to discharge the blood from an outlet port;
    a valve mechanism having a first input port, a second input port, a first output port and a second output port wherein one of said first and second input ports is configured to connect to one of the right and left atriums and the other of said first and second input ports is configured to connect to the other of the right and left atriums and wherein one of the first and second output ports is configured to connect to one of the pulmonary artery and aorta and the other of the first and second output ports is configured to connect to the other of the pulmonary artery and aorta;
    said valve mechanism comprising:
    a first switching valve disposed between the inlet port of said pump and said first input port;
    a second switching valve disposed between the inlet port of said pump and said second input port;
    a third switching valve disposed between the outlet port of said pump and said first output port;
    a fourth switching valve disposed between the outlet port of said pump and said second output port; and
    control means for actuating said first switching valve to allow blood flow therethrough and synchronously actuating said third switching valve to allow blood flow therethrough while blocking blood flow in said second and fourth switching valves, said control means actuating said second switching valve to allow blood flow therethrough and synchronously actuating said fourth switching valve to allow blood flow therethrough while blocking blood flow in said first and third switching valves.

2. An artificial heart according to claim 1, wherein said valve mechanism comprises a cylinder and a valve spool slidably disposed in said cylinder, said cylinder being formed with ports fluidically connected to the inlet port and outlet port of said pump and being formed with said first input port, second input port, first output port and second output port.

3. An artificial heart according to claim 2, wherein said valve mechanism further comprises an electromagnetic actuator for actuating said valve spool to reciprocate within said cylinder.

4. An artificial hear according to claim 1, wherein said pump is a centrifugal pump comprising a housing, a motor rotatably disposed in said housing, and a motor connected to said rotor for rotating said rotor.

5. An artificial heart according to claim 1, wherein said control means actuates said third switching valve with a predetermined time delay after the actuation of said first switching valve and actuates said fourth switching valve with a predetermined time delay after the actuation of said second switching valve.

6. An artificial heart according to claim 1, wherein said control means actuates said first and third switching valves simultaneously and actuates said second and fourth switching valves simultaneously.

7. An artificial heart for the circulatory system of a human body consisting essentially of:

a single one-way pump configured to introduce blood through an inlet port and to discharge the blood from an outlet port;

a mechanism having a first input port, a second input port, a first output port and a second output port wherein said first input port is configured to connect to the right atrium, the second input port is configured to connect to the left atrium, the first output port is configured to connect the pulmonary artery and the second output port is configured to connect to the aorta;

said valve mechanism comprising:

a first switching valve disposed between the inlet port of said pump and said first input port;

a second switching valve disposed between the inlet port of said pump and said second input port;

a third switching valve disposed between the outlet port of said pump and said first output port;

a fourth switching valve disposed between the outlet port of said pump and said second output port; and control means for actuating said first switching valve to allow blood flow therethrough and synchronously actuating said third switching valve to allow blood flow therethrough while blocking blood flow in said second and fourth switching valves, said control means actuating said second switching valve to allow blood flow therethrough and synchronously actuating said fourth switching valve to allow blood flow therethrough while blocking blood flow in said first and third switching valves.

* * * * *